United States Patent [19]
Krbechek

[11] Patent Number: 6,077,970
[45] Date of Patent: Jun. 20, 2000

[54] CARBOXYLIC ACID ESTERS OF 2-HYDROXY-5-ISOALKYL-BETA-METHYLSTYRENE

[75] Inventor: Leroy Krbechek, Santa Rosa, Calif.

[73] Assignee: Henkel Corporation, Gulph Mills, Pa.

[21] Appl. No.: 09/166,563

[22] Filed: Oct. 6, 1998

Related U.S. Application Data

[62] Division of application No. 08/912,009, Aug. 15, 1997, Pat. No. 5,877,355, which is a continuation of application No. 08/670,127, Jun. 25, 1996, abandoned, which is a continuation-in-part of application No. 08/635,865, Apr. 23, 1996, which is a continuation-in-part of application No. 08/622,337, Mar. 21, 1996, abandoned, which is a continuation-in-part of application No. 08/616,501, Mar. 19, 1996, abandoned.

[51] Int. Cl.$^7$ ................................................. C07C 69/017
[52] U.S. Cl. ........................ 560/251; 560/129; 560/130; 560/143
[58] Field of Search ........................... 585/435; 568/430, 568/432; 560/130, 143, 129, 256

[56] References Cited

U.S. PATENT DOCUMENTS

| | | | |
|---|---|---|---|
| 3,173,956 | 3/1965 | Grinstead | 260/600 |
| 3,206,513 | 9/1965 | Budde | 260/600 |
| 3,224,873 | 12/1965 | Swanson | 75/101 |
| 3,321,526 | 5/1967 | Marchand | 260/600 |
| 3,423,449 | 1/1969 | Burk, Jr. et al. | 260/453 |
| 3,592,775 | 7/1971 | Swanson | 252/182 |
| 3,673,257 | 6/1972 | Di Bella | 260/600 |
| 3,780,110 | 12/1973 | Gay et al. | 260/600 |
| 3,972,945 | 8/1976 | Albright | 260/600 R |
| 4,020,105 | 4/1977 | Ackerley et al. | 260/566 |
| 4,020,106 | 4/1977 | Ackerley et al. | 260/566 A |
| 4,026,950 | 5/1977 | Le Ludec | 260/600 R |
| 4,085,146 | 4/1978 | Beswick | 260/600 R |
| 4,124,643 | 11/1978 | Martan et al. | 260/600 R |
| 4,142,952 | 3/1979 | Dalton | 204/106 |
| 4,151,201 | 4/1979 | Casnati et al. | 260/562 A |
| 4,190,605 | 2/1980 | Muench et al. | 260/600 R |
| 4,231,967 | 11/1980 | Matsuda et al. | 568/433 |
| 4,324,922 | 4/1982 | Smith | 568/437 |
| 4,377,555 | 3/1983 | Hancock | 423/6 |
| 4,507,268 | 3/1985 | Kordosky et al. | 423/24 |
| 4,638,096 | 1/1987 | Virnig | 568/433 |
| 4,868,334 | 9/1989 | Mathew et al. | 564/264 |
| 5,300,689 | 4/1994 | Krbechek et al. | 564/259 |

FOREIGN PATENT DOCUMENTS

| | | |
|---|---|---|
| 4104835 | 8/1991 | Germany . |
| 54-26900 | 2/1979 | Japan . |

OTHER PUBLICATIONS

Allied Signal Chemicals, "MOC –55 Extractant" Product Data sheets, 3 pages, 1994.

R. E. Ford et al. : "Synthesis and quantitative structure–activity relationships of antiallergic 2–hydroxy–N–1H–tetrazol–5–benzamides", J. Med. Chem., vol. 29, 1986, pp. 538–549 XP002109293.

Ferguson, "The Synthesis of Aromatic Aldehydes", *Chemical Reviews*, vol. 38, pp. 227–254 (1946).

Parrish, "Derivatives of Salicylaldoxime", *Journal of the South African Chemical Institute*, vol. XXIII, pp. 129–135, (1970).

Wynberg, "The Reimer–Tiemann Reaction", *Chemical Reviews*, vol. 60, pp. 169–184 (1960).

Krbechek, L., Labatory Notebook No. 7510, p. 47, Jun. 6, 1994.

Krbechek, L., Laboratory Notebook No. 7537, p. 46, Feb. 8, 1994.

*Primary Examiner*—Sreeni Padmanabhan
*Attorney, Agent, or Firm*—John E. Drach; Frank E. Robbins; Garrett V. Davis

[57] ABSTRACT

The present invention relates to carboxylic acid esters of 2-hydroxy-5-isoalkyl-beta-methylstyrenes wherein the said isoalkyl substituent comprises 8–18 carbon atoms.

5 Claims, 1 Drawing Sheet

CARBOXYLIC ACID ESTERS OF 2-HYDROXY-5-ISOALKYL-BETA-METHYLSTYRENE

CROSS REFERENCE TO RELATED APPLICATION

This application is a divisional application of Ser. No. 08/912,009, filed Aug. 15, 1997, now U.S. Pat. No. 5,877,355, which is a continuation of Ser. No. 08/670,127 filed Jun. 25, 1996, now abandoned, which is a continuation-in-part of Ser. No. 08/635,865 filed Apr. 23, 1996 which is a continuation-in-part of Ser. No. 08/622,337 filed Mar. 21, 1996 (now abandoned) which is a continuation-in-part of Ser. No. 08/616,501 filed Mar. 19, 1996 (now abandoned).

BACKGROUND OF THE INVENTION

This invention relates to a process for the preparation of hydroxyarylaldehydes from 4-alkylphenols by a new route. The invention further relates to the novel compositions that are prepared from the 4-alkylphenols. Among other uses known in the art, hydroxyarylaldehydes are particularly useful as intermediates in the preparation of oximes which find utility as metal extractants.

The end compounds produced by the processes of the present invention are particularly useful as intermediates for the production of oximes that in turn are useful for the extraction of copper and other metals from aqueous solutions. In this recovery process, the metal extractant is dissolved in a solvent, and is contacted with an aqueous metal solution to form a complex with the metal which is soluble in an organic solvent. The organic phase is then separated from the aqueous phase and the metal is stripped from the organic phase, usually by means of an acid.

The water immiscible solvents usually employed for this purpose are hydrocarbon solvents such as the petroleum-derived liquid hydrocarbons, either straight chain or branched, such as kerosene, fuel oil, etc. Various aromatic solvents may also be used, such as, for example, benzene, toluene, xylene and other aromatic solvents, particularly those derived from petroleum processing which may contain alkyl substituted aromatic materials. In addition to the simple hydrocarbon solvents, the chlorinated hydrocarbons may also be used and in some instances may improve solubility. Accordingly, both the unsubstituted and the chlorinated solvents are contemplated by the term "liquid hydrocarbon".

The extractants that are made from the intermediates that are produced by the processes of the present invention are characterized as having sufficient solubility in one or more of the above solvents or mixtures thereof to make about a 2% solution, and they are essentially insoluble or immiscible with water. At the same time, they each should form a complex with a metal, such as copper, which complex, likewise, is soluble in the organic solvent to at least the extent of about 2% by weight.

These characteristics are generally achieved by having alkyl substituents on the ring, that have at least 3 alkyl carbon atoms. Usually it is preferred not to have more than 25 carbon atoms total in the alkyl substituents since these substituents contribute to the molecular weight of the oxime extractant without improving operability. Large substituents, also, increase the amount of oxime needed for a given copper loading capacity. In general, the branched chain alkyl substituents effect a greater degree of solubility of the reagent and of the copper complex and, accordingly, these are preferred, especially those of 6 to 18 carbons.

As described in U.S. Pat. No. 4,868,334, for example, oxime extractants are often produced by reacting an organic carbonyl compound such as an aldehyde or ketone with hydroxylamine, usually generated from a hydroxylamine salt such as hydroxylammonium sulfate or hydroxylammonium chloride.

Current oximation procedures employ standard oximation processes with an alcohol such as methanol as a solvent, hydroxylammonium sulfate, and sodium acetate. An improved oximation process is described, for example, in U.S. Pat. No. 5,300,689.

The oximes, such as the hydroxy aryl ketoximes and hydroxy aryl aldoximes, which are substantially insoluble in water but soluble in water-immiscible organic solvents, such as kerosene, are useful in solvent extraction processes for the recovery of metals, particularly copper, from aqueous solutions. U.S. Pat. No. 4,507,268 describes a number of such oxime reagents prepared from ketones and aldehydes, and the use thereof in liquid/liquid extraction processes.

Reagents frequently employed in commercial processes for copper recovery are included among those offered by Henkel Corporation under the LIX® trademark, viz., LIX®63, LIX®065N, LIX®64, LIX®64N, LIX®70, LIX®71, LIX®73, LIX®34, LIX®54, LIX®605, LIX®617, LIX®622 and LIX®6022, LIX®860, LIX®984, LIX®973, and LIX®84.

Briefly noted, LIX®63 extractant includes, in addition to a liquid hydrocarbon diluent, an aliphatic α-hydroxy oxime extractant (5,8-diethyl-7-hydroxy-dodecan-6-oxime) of the type illustrated in Swanson U.S. Pat. No. 3,224,873. The LIX®65N extractant includes an alkyl substituted hydroxy benzophenone oxime (2-hydroxy-5-nonyl benzophenone oxime) as set out in Swanson U.S. Pat. No. 3,592,775. The LIX®64 extractant and the LIX®64N extractant incorporate benzophenone oxime extractants (2-hydroxy-5-dodecyl benzophenone oxime and 2-hydroxy-5-nonyl benzophenone oxime, respectively) in combination with an aliphatic α-hydroxy oxime as described in U.S. Pat. No. 3,423,449.

Formulation of the LIX®70 extractant involves the combination of a benzophenone oxime extractant containing an electron withdrawing substituent (2-hydroxy-3-chloro-5-nonyl benzophenone oxime) with an aliphatic α-hydroxy oxime. The LIX®71 and LIX®73 formulations both include a mixture of two benzophenone oximes, one of which has an electron withdrawing substituent (i.e., a mixture of 2-hydroxy-5-nonyl benzophenone oxime and 2-hydroxy-3-chloro-5-nonyl benzophenone oxime) with the latter reagent further including an aliphatic α-hydroxy oxime.

The LIX®34 extractant and the LIX®54 extractant incorporate alkaryl sulfonamido quinoline and β-diketone extractants, respectively. The LIX®605 extractant, the LIX®617 extractant, the LIX®622 extractant, and the LIX®6022 extractant, on the other hand, employ alkyl substituted hydroxy benzaldoxime (salicylaldoxime) extractants according to Parrish, *J. South African Chem. Inst.,* 23, pp. 129–135 (1970). Thus, the LIX®605 extractant and the LIX®617 extractant include 2-hydroxy-5-nonyl benzaldoxime extractants with, respectively, nonylphenol and tridecanol additives. The LIX®622 extractant and the LIX®6022 extractant comprise formulations of 2-hydroxy-5-dodecyl benzaldoxime and a tridecanol additive in approximately 4:1 and 1:1 w/w ratios, respectively. Acorga PT-5050 extractant is offered for sale by Acorga, Ltd., Hamilton, Bermuda, as a formulation comprising 2-hydroxy-5-nonyl benzaldoxime and a tridecanol additive in an approximately 2:1 w/w ratio. See also, Ackerley et al., U.S. Pat. No. 4,020,105; Ackerley et al., U.S. Pat. No. 4,020,106; and Dalton, U.S. Pat. No. 4,142,952.

There exists a general need in the art for more efficient processes for producing such oxime extractants. In the usual processes, the hydroxyarylaldehydes may be prepared by a number of routes. A summary and review of the synthesis of aromatic hydroxyarylaldehydes may be found in H. Fiege, K. Wedemehyer, K. A. Bauer, A. Krempel and R. G. Molleken, Fragrance Flavor Subst. Proc. Int. Haarmann Reimer Symp. 2nd, 1979 (Publ. 1980), pp. 63–73, which discusses in particular three processes of preparation.

One of these processes is the Reimer-Tiemann reaction which involves the reaction of a phenol with chloroform under very basic conditions to yield the salicyaldehyde. Yields tend to be low and recovery of the product difficult. U.S. Pat. No. 4,324,922 relates to improvements in the process, citing as further background Hans Wynberg, "Chemical Reviews", Vol. 60, 169 (1960) and Ferguson, "Chemical Reviews", Vol. 38, 229 (1946). Other U.S. patents, U.S. Pat. No. 3,206,513 and 3,972,945, provide further background.

A second industrially useful approach involves condensation of the phenol with formaldehyde followed by oxidation with oxygen and a catalyst. While reasonable yields of salicylaldehyde are obtained, the process consists of two steps and involves the use of expensive catalysts. Illustrative of some of the patents relating to this process are U.S. Pat. Nos. 3,173,956, 3,321,526, 3,673,257, 3,780,110, 4,026,950 and 4,190,605.

Other variations have been introduced. One which is described in U.S. Pat. No. 4,151,201, involves heating paraformaldehyde with phenol in the presence of anhydrous stannous chloride and pyridine. A second, which is described in U.S. Pat. No. 4,231,967, involves replacing the stannous chloride with an iron or chromium compound, preferably chromium acetylacetonate. Good yields are obtained via both processes. Both processes require relatively high levels of the catalyst promoter, pyridine, which must be recycled and requires special handling on an industrial scale. The use of heavy metals also presents problems in waste disposal. Further, iron and chromium compounds tend to promote adverse side reactions. A third variation which is described in U.S. Pat. No. 4,638,096, involves reacting a corresponding phenolic compound with formaldehyde in the presence of a titanium or zirconium containing catalyst.

Another process, disclosed in U.S. Pat. No. 4,085,146 directed specifically towards production of alkylsalicylaldehydes, involves formation of a Mannich base, followed by oxidation and hydrolysis to the alkyl-salicylaldehyde. While good yields are said to be obtained, the process is economically burdensome due to the number of steps involved.

It is an object of the instant invention to provide a new process for making substituted hydroxyaryl aldehydes, particularly, alkyl substituted salicylaldehydes, which process affords substantial product yields.

SUMMARY OF THE INVENTION

In one preferred embodiment, the invention relates to novel processes for the production of substituted hydroxyarylaldehydes (substituted salicylaldeydes) which, after oximation, are useful metal extractants.

In another embodiment, the invention relates to novel precursors that are produced during the reaction steps of the above preferred embodiment processes. More specifically, the invention relates to precursors that are useful in the synthesis of hydroxyarylaldehydes, such as, for example, 4-isoalkylphenyl allyl ethers; 2-allyl-4-isoalkylphenols; and 2-hydroxy-5-isoalkyl-beta-methylstyrenes. In another and related embodiment, the invention relates to processes for making each of these and other novel precursors useful in the production of hydroxyarylaldehydes, and particularly, 5-alkyl salicylaldehydes.

In still another embodiment, the invention relates to a process comprising the ozonization of solutions of 2-hydroxy-5-alkyl-beta-methylstyrenes, whereby substantial amounts of 5-alkyl-substituted salicylaldehydes are formed, and from which the desired metal extractants may be produced by oximation.

DETAILED DESCRIPTION OF THE INVENTION

Figure 1:
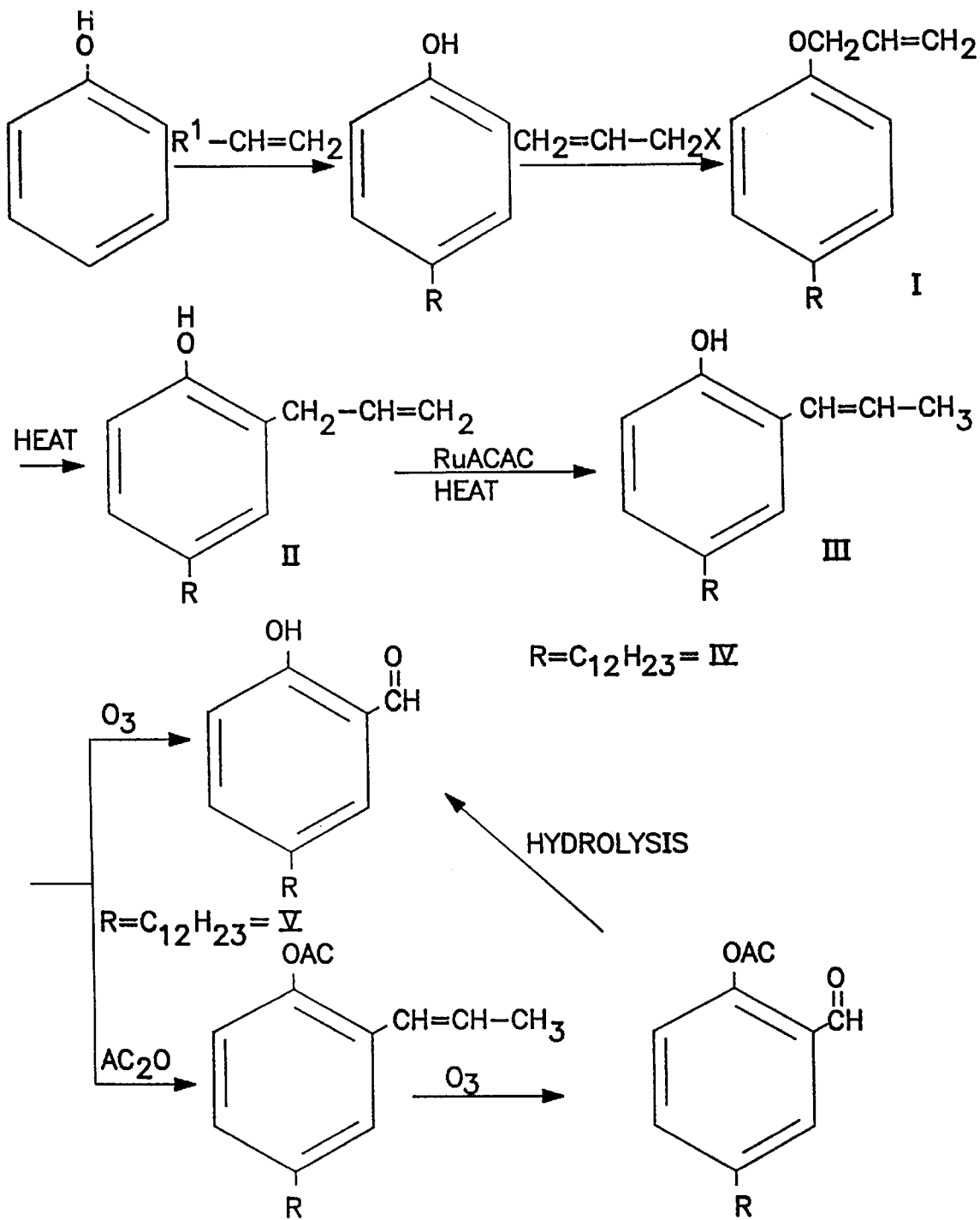
FIG. 1 is a schematic diagram illustrating new processes for the preparation of substituted hydroxyaryl aldehydes, especially alkyl substituted salicylaldehydes that are useful intermediates in the production of metal extractants.

The process of the invention uses 4-alkylphenols as starting materials. Preferably, the starting materials are 4-isoalkylphenols. However, the alkyl moiety in the starting material can be a straight chain alkyl, or other alkyl isomer. In the following discussion, for simplicity's sake, it is generally assumed that preferred starting materials are used.

The 4-alkylphenols are and can be manufactured by the alkylation of phenol with olefins as shown as a first reaction step in FIG. 1 of the drawing. Suitable olefins are: octenes; nonenes including tripropylenes; decenes; undecenes; dodecenes including triisobutylenes; tetraisopropylenes; tridecenes; and so on. Since the preferred alkyl-substituted salicylaldehydes are those with isoalkyl substitution, it is preferred that this step produce a 4-isoalkyl phenol, such as, for example, a phenol substituted in the 4 position with an isononyl or an isododecyl substituent.

As illustrated in FIG. 1, the alkylphenols are then alkylated at the phenolic oxygen atom with allyl derivatives, to produce the corresponding allyl ethers (I), preferably the 4-isoalkylphenyl allyl ethers (I). The allyl ethers are rearranged via the classical Claisen rearrangement, by heating to a temperature in the range from about 140° C. to about 220° C., to the corresponding 2-allyl-4-alkylphenols (II), which are then isomerized to 2-hydroxy-5-alkyl beta-methylstyrenes (III).

These suitably alkyl-substituted styrenes, or their derivatives, are then cleaved at the propenyl moiety, to produce the corresponding alkyl substituted benzaldehydes. The cleavage is accomplished by ozonolysis. When the 2-hydroxy-5-alkyl beta-methylstyrene is subjected to ozonolysis in methanol, and the ozonized solution is then reduced with 0.1 molar sodium thiosulfate, and the product is isolated, TLC indicates that the major component present is 5-alkyl salicylaldehyde.

When the ozonolysis is carried out on a solution of the 2-acetoxy-5-alkyl beta-methylstyrene in glacial acetic acid, the acetate functionality is not affected by the ozonolysis, but the beta-methylstyrene substituent is converted to an aldehyde group, —CHO, and the acetate group can then be removed by hydrolysis. The final product is a 5-alkyl salicylaldehyde, again present as the major component. The alkyl substituted benzaldehydes per se or their hydrolysates are substituted salicylaldehydes, which, after oximation, are useful metal extractants.

The ozonolysis can be carried out in a number of solvents including alcohols such as methanol, ethanol or isopropanol; ketones such as acetone; hydrocarbons such as toluene or heptane; carboxylic acids such as acetic acid; esters such as butyl acetate, and ethers such as dimethoxyethane or tetrahydrofuran.

The reactions of the invention are generally straightforward and may be repeated fairly easily by those with skill in the art.

In the following examples that demonstrate the invention, the allyl derivative used to produce the first precursor (I) was allyl chloride ($H_2C=CHCH_2Cl$). However, other allyl compounds such as allyl bromide, allyl iodide, and allyl sulfate can be used as well as corresponding substituted allyl compounds.

Ruthenium acetylacetonate, a precious metal complex, was used to isomerize precursor II. Other precious metal complexes or supported precious metal catalysts may be used to isomerize precursor II. For instance, five percent ruthenium on carbon may be used instead of ruthenium acetylacetonate.

The processes and products of the invention will now be described with reference to the schematic diagram shown in FIG. 1.

Except in the operating examples below, all numbers expressing quantities of ingredients or reaction conditions are understood to be modified by the word "about". Throughout, all parts and percentages are by weight, unless expressly indicated to be otherwise. All temperatures are in degrees Celsius unless expressly stated otherwise.

Example 1 below describes the preparation of the 4-alkylphenyl allyl ether of Product I. Example 2 describes the preparation of Product II, a 2-allyl-4-alkylphenol, from Product I. Example 3 describes the production of a beta-methylstyrene.

Examples 4–10 each describe one of the steps that were used to make the desired final desired product, a substituted salicylaldehyde.

Lastly, the oximation of Product IV is described in Example 10.

EXAMPLE 1

Preparation of p-isododecylphenyl allyl ether (I)

273 grams (1.042M) p-isododecylphenol in 300 ml of toluene, 17.7 grams of tetra butyl ammonium hydrogen sulfate, and 395 grams of 50% NaOH aqueous solution were reacted together to give a semisolid material; and then heated to 60° C., when this initial reaction product became fluid.

Next, 363 grams (4.75M) of allyl chloride were added, and mixed with the fluid initial reaction product. The mixture was then heated to 63° C., and exothermed slowly to 73° C. A sample was taken at this point, then acidified and stripped under reduced pressure. TLC revealed the presence on the sample of a small amount of unreacted p-isododecylphenol.

The temperature of the mixture was then held at 75° C. for 8 hours. During this period of time, periodic TLC analyses indicated that the content of unreacted isododecylphenol gradually decreased. At the four hour mark, the TLC analysis indicated that a trade of the isododecylphenol remained. GC/IR revealed that the product was mostly the 4-isododecylphenyl allyl ether, together with the unreacted isododecylphenol, and a small amount of ortho isododecylphenol.

The reaction mixture, at the end of the 8 hours of maintained temperature, was washed with water, then washed with sulfuric acid, then again with water. The reaction had not gone to completion.

Next, 12 grams of 50% sodium hydroxide aqueous solution and 11.5 grams of allyl chloride were added, mixed in, heated to 75° C., and allowed to react for 3 more hours for a total of 11 hours. The 11 hour product in sequence was washed with water, the aqueous layer formed being discarded, washed with $H_2SO_4$, and then washed with water three more times. After each washing, the aqueous layer formed was discarded. Then the end product was stripped under reduced pressure, and 316 grams of end product were recovered.

Gas chromatography/infra red (GC/IR) analysis showed that the end product comprised only 1–2% of isododecylphenol, 1–2% of a diallyl isomer, and that the primary constituent was p-isododecylphenyl allyl ether (I).

EXAMPLE 2

Preparation of 2-hydroxy-5-isododecyl allyl benzene (II)

All of the end product I recovered in Example 1 was heated at 210° C.–215° C. for 8 hours, then distilled using a vacuum jacketed packed column. Several fractions were taken using the vacuum jacketed packed column, a first one at BP 115° C.–150° C. at 2 mm pressure. Analysis of the 8.3 g product by GC/IR. indicated the presence of about 9% of aliphatic hydrocarbon, about 1.5% as alkyl substituted diallyl phenol where the alkyl has many fewer than 12 carbons, about 30% ortho nonyl phenol, and about 50% of the desired product, 2-hydroxy 5-isododecyl allyl benzene.

A second fraction was taken off under 2 mm pressure, at 150°–165° C. GC/IR analysis of this fraction indicated that it contained about 98% of the desired product, i.e. 2-hydroxy 5-isododecyl allyl benzene.

A third fraction, taken under 2 mm pressure, at 165°–170° C., analyzed about 91% of the desired product, and about 9% 2-hydroxy 5-isododecyl diallyl benzene. These fractions, when taken together, yielded 251 grams, of which 97% by weight was 2-hydroxy-5-dodecyl allyl benzene (II).

EXAMPLE 3

Preparation of 2-hydroxy-5-isododecyl-beta-methylstyrene

The product of Example 2, 2-allyl 4-isododecyl phenol was isomerized to produce 2-hydroxy-5-isododecyl beta-methylstyrene. This involved making up a mixture consisting of 125 g of 2-allyl 4-isododecyl phenol and 0.25 g of ruthenium acetylacetonate by stirring them together at 130° C. under a nitrogen atmosphere for 8 hours.

The resulting reaction mixture was distilled and a fraction was taken in a temperature range of 150° C. –155° C. at 90 micrometers pressure, to produce 93 g of distillate material. This distillate material, upon analysis by GC/IR, appeared to be about 95% 2-hydroxy 5-isododecyl beta-methylstyrene.

Preparations of Substituted Salicylaldehydes from 2-hydroxy-5-dodecyl-beta-methylstyrene (III)

The following five examples demonstrate the preparation of substituted salicylaldehydes from 2-hydroxy-5-isododecyl-beta-methylstyrene (IV).

EXAMPLE 4

Ozonolysis in the Presence of Glacial Acetic Acid

A solution of 6.19 grams of 2-hydroxy-5-isododecyl-beta-methylstyrene (III where R=$C_{12}H_{25}$) in about 150 ml of glacial acetic acid was ozonized at 20–25° C., using gaseous ozone bubbled through the solution, until no more starting material was detected by thin layer chromatography (TLC), using silica gel, 75% toluene, and 25% heptane.

The resultant mixture was reduced with Zn dust to reduce any peroxides, hydroperoxides, ozonides, etc., by stirring for 15 minutes at 40°–45° C. This mixture was then diluted with water and extracted two times with toluene. The combined toluene extracts were washed two times with water, after which the volatiles were removed at reduced pressure to leave a residue of 6.1 grams. Analysis by TLC showed the major component present to be 5-isododecylsalicylaldehyde (V) (DSA).

Analysis by thin film Infra Red (IR) showed the product to contain about 80% 5-isododecylsalicylaldehyde (DSA).

EXAMPLE 5

Ozonolysis of Compound IV in Methanol

The ozonolysis was repeated by bubbling gaseous ozone through a solution of 6.25 grams of compound IV in about 150 ml of methanol. Compound IV is compound III where $R=C_{12}H_{25}$ is isododecyl. The ozonized solution was reduced with 0.1 molar sodium thiosulfate and the product isolated to yield 6.0 grams of material. Analysis by TLC showed the major component present to be DSA. Analysis by IR showed the product to contain about 67% DSA.

EXAMPLE 6

Ozonolysis of Compound IV in Acetone

The ozonolysis was conducted on a solution of 6.10 grams of compound IV in about 150 ml of acetone. The product was isolated, with a yield of 6.0 grams of product, which also was rich in DSA by TLC analysis. Analysis by IR showed that the product contained about 77% DSA.

EXAMPLE 7

Ozonolysis of Compound IV in Toluene

The ozonolysis was conducted on a solution of 6.10 grams of compound IV in about 150 ml of toluene. Again the product was isolated to yield 6.7 grams of material which was also rich in DSA by TLC analysis. Analysis by IR showed that the product contained about 59% DSA.

EXAMPLE 8

Ozonolysis of Compound IV in Heptane

The ozonolysis was conducted on a solution of 6.07 grams of compound IV in about 150 ml of heptane. The product was isolated, with a yield of 6.8 grams of residue which is rich in DSA by TLC analysis. Analysis by IR showed that the product contained about 54.5% DSA.

EXAMPLE 9

Production of DSA by a Two Step Process in which Compound IV is First Ozonized in Glacial Acetic Acid in Step One, Then Hydrolyzed in Step Two Step 1

In the first phase of this example, a solution consisting of 6.9 grams of 2-acetoxy-5-isododecyl-beta-methylstyrene, compound VI, in about 150 ml of glacial acetic acid, was ozonized by passing gaseous ozone through the solution at about 20° C., until no more starting material was detected by TLC. The reaction mixture was reduced with zinc dust at 40°–45° C. for about 15 minutes.

The resultant mixture was then diluted with water, extracted two times with toluene and the combined toluene, extracts washed two times with water. The volatiles were then removed at reduced pressure to leave 6.7 grams of residue.

Thin film infra red analysis showed the product to contain DSA with some DSA acetate.

Step 2

In the second phase of this example, the crude product residue from Step 1 was stirred at room temperature for 48 hours in about 50 ml of methanol which contained 2.4 grams of 50% sodium hydroxide. The reaction mixture was then acidified with aqueous sulfuric acid and extracted two times with toluene.

The toluene extracts were combined, washed two times with water, then stripped of volatiles at reduced pressure, to leave 5.35 grams of material which TLC showed to contain a substantial amount of DSA. Analysis by IR showed the product to contain about 77% DSA.

EXAMPLE 10

Oximation of Crude DSA and Demonstration of Copper Extraction

A mixture consisting of 2.60 grams of the product of Ex. 4, 1.4 grams of hydroxylamine sulfate, 1.5 grams of sodium acetate, and about 25 ml of methanol, was heated at reflux temperature for 5.5 hours. Analysis by TLC showed no detectable residual DSA.

The reaction mixture was then diluted with water and extracted with toluene. This toluene extract was washed two times with water before the toluene was removed at reduced pressure to leave 2.64 grams of residue. Analysis by IR showed the oximation to be substantially complete.

After removal of the analytical sample, the remaining oxime was dissolved in 48 ml of SX-11 kerosene. This kerosene solution was shaken for 10 minutes with 25 ml aqueous copper sulfate solution which contained 7.01 grams of copper per liter. After extraction of the copper, the aqueous raffinate contained only 0.74 grams of copper per liter.

Conclusion

The purpose of the alkyl substituents on the ring of both the intermediate compounds with the production of which this invention is concerned, and the final oxime extractants themselves, is to enhance solubility in organic solvents. Consequently, the alkyl substitution preferably consists of a substituent inserted or attached to the ring at one location, providing a long chain that will enhance solubility, and that preferably is an isoalkyl, to optimize solubility. Since the size of the alkyl substituent increases the molecular weight of the metal extractant, the shorter the chain the better, consistent with enhanced solubility.

While the invention has been illustrated with reference to the use of an isododecyl alkyl substituent at the 4 position on the ring of the initial alkyl phenol reactant, and also as present in the metal extractant, other substituted alkyl chains, and particularly isoalkyl chains, can be used. The respective efficacy of a particular substituent in a particular metal extractant may depend upon the conditions under which the particular metal extractant is to be used.

Although the invention has been illustrated with reference to the use of an isododecyl alkyl substituent at the 4 position on the ring of the initial alkyl phenol reactant, it will be understood by those with skill in the chemical arts that many, many other alkyl chains can be substituted for isododecyl alkyl to thereby create other new compositions of the invention.

For instance, some of the new compositions of the invention can be represented as follows:

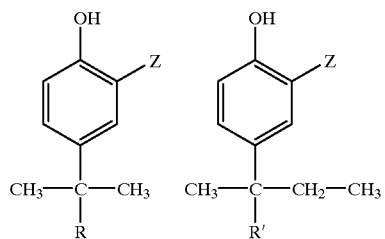

where
R=isohexyl or isononyl
R'=isopentyl or isooctyl
Z=allyl or 2 propenyl.

In addition, other new compositions of the invention can be represented as

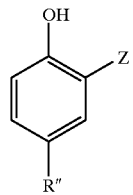

where R" is a straight chain octyl, nonyl or decyl alkyl and wherein R" is attached to the ring by way of any carbon atom making up R".

Other products of the invention include the use of a totally branched octyl substituent (i.e., 1,1,3,3-tetra methyl butyl) or a highly branched nonyl or a highly branched decyl substituent and mixtures thereof.

In short, there are many products taught by the invention which are new although they may not be described herein in detail. Mixtures of two or more of the new products are, of course, also new and useful.

The salicylaldehydes that can be produced by the invention provide, at present, relatively inexpensive materials for oximation, for the production of metal extractants. The initial raw materials are readily available and the reaction steps of the present invention are straightforward.

While the invention has been described in connection with particular embodiments thereof, it should be understood that the invention is not confined to what has been demonstrated in this application to be useful, and the invention is one of broad scope as defined in the appended claims.

What is claimed is:

1. A carboxylic acid ester of 2-hydroxy 5-isoalkyl beta-methylstyrene, wherein said isoalkyl group has at least 8 carbon atoms.

2. The compounds of claim 1 wherein said isoalkyl group has up to 18 carbon atoms and said carboxylic acid has 2–6 carbons.

3. The compounds of claim 2 wherein said isoalkyl substituent comprises isononyl or isododecyl.

4. The acetic acid ester of a 2-hydroxy 5-isoalkyl beta-methylstyrene.

5. The ester of claim 4 wherein said isoalkyl substituent comprises an isoalkyl substituent that has 8 to 18 carbons.

* * * * *